United States Patent [19]
Herrmann et al.

[11] Patent Number: 6,025,496
[45] Date of Patent: Feb. 15, 2000

[54] PROCESS FOR PREPARING HETEROCYCLIC CARBENES

[75] Inventors: Wolfgang A. Herrmann, Freising; Christian Kocher; Lukas Goossen, both of Munich, all of Germany

[73] Assignee: Celanese GmbH, Germany

[21] Appl. No.: 09/155,065

[22] PCT Filed: Mar. 14, 1997

[86] PCT No.: PCT/EP97/01296

§ 371 Date: Nov. 2, 1998

§ 102(e) Date: Nov. 2, 1998

[87] PCT Pub. No.: WO97/34875

PCT Pub. Date: Sep. 25, 1997

[30] Foreign Application Priority Data

Mar. 20, 1996 [DE] Germany .................. 196 10 908

[51] Int. Cl.[7] ................. C07D 233/10; C07D 233/12; C07D 233/14; C07D 233/16; C07D 249/08
[52] U.S. Cl. ............... 548/107; 548/264.2; 548/264.6; 548/300.1; 548/347.1
[58] Field of Search .............. 548/300.1, 347.1, 548/264.6, 107, 264.2

[56] References Cited

U.S. PATENT DOCUMENTS

| | | | |
|---|---|---|---|
| 5,386,062 | 1/1995 | Teles et al. | 568/463 |
| 5,508,422 | 4/1996 | Teles et al. | 548/264.2 |
| 5,585,496 | 12/1996 | Teles et al. | 548/264.2 |
| 5,728,839 | 3/1998 | Herrmann et al. | 548/103 |

FOREIGN PATENT DOCUMENTS 0587044  3/1994  European Pat. Off. .

OTHER PUBLICATIONS

Journal of American Chemical Society, Sep. 1, 1992, pp. 5530 to 5534, vol. 114, No. 14 (5 pages) Arduengo et al.

Angewandte Chemie 1995 vol. 34, No. 9, May 15, 1995 (3 pgs), Enders et al.

Primary Examiner—Floyd D. Higel
Attorney, Agent, or Firm—Bierman, Muserlian and Lucas

[57] ABSTRACT

A process for preparing heterocyclic carbenes of the

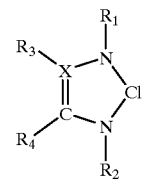

in which $R^1$, $R^2$, $R^3$ and $R^4$ are individually saturated or unsaturated, straight chain, branched or cyclic, unsubstituted or substituted $C_1$–$C_{10}$ alkyl, $C_2$–$C_5$ alkylidene, $C_2$–$C_5$ alkylidine, $C_7$–$C_{19}$ aralkyl or $C_6$–$C_{14}$ alkyl groups, $R^3$ and $R^4$ can also stand for hydrogen or form jointly anellated, substituted or unsubstituted groups with between 3 and 7 carbon atoms and X stands for carbon or nitrogen, $R^3$ being dropped if X is nitrogen comprising reacting azolium salts with a deprotonizing reagent in pure liquid ammonia or in pure organic amine or a mixture of liquid ammonia or an organic amine and an organic polar-aprotic solvent which are a plurality of temperature-sensitive carbenes are produced under mild reaction conditions at temperatures of between −75 and 0° C.

9 Claims, No Drawings

PROCESS FOR PREPARING HETEROCYCLIC CARBENES

This application is as 371 of PCT/EP97/01296 filed Mar. 14, 1997.

Heterocyclic carbenes have in recent times been found to be useful as complexing ligands for a wide variety of metals, with the corresponding metal complexes having a high thermal and chemical stability and very good catalyst properties in the homogeneous catalysis of various reactions.

Metal complexes of metals of metals of the 8th, 9th and 10th groups of the Period Table containing heterocyclic monocarbenes or dicarbenes as ligands are described, for example, in the European Patent Application No. 0 719 753 as suitable catalysts for reactions leading to the formation of carbon-carbon, carbon-hydrogen and carbon-silicon bonds. Furthermore, in the German Patent Application number P 44 47 067.3, cobalt or rhodium complexes having heterocyclic monocarbene or dicarbene ligands are used as catalysts for the hydroformylation of olefinically unsaturated compounds to give aldehydes.

According to the European Patent Application 0 719 758, it is also possible to prepare aromatic olefins from haloaromatics and olefins via a Heck reaction in the presence, as catalysts, of palladium complexes containing heterocyclic carbenes as ligands.

Furthermore, the German Patent Application number P 44 47 070.3 discloses the use of complexes of the lanthanides having heterocyclic carbenes as complexing ligands as catalysts for reactions which are catalyzed by Lewis acids, e.g. for preparing polylactides, and for various CH, CC, CSi and NC linkage reactions.

Metal complexes of heterocyclic carbenes thus have a wide range of catalytic applications; the synthesis of these compounds is therefore of great importance. On this subject, one is frequently directed to the free heterocyclic carbenes whose preparation has, however, hitherto been tied to very specific reaction conditions which greatly restrict the variety of classes of materials which can be used as starting material. Thus, according to the known synthetic methods, only a comparatively small selection of heterocyclic carbenes has hitherto been obtainable, in particular 1,3-dimethylimidazolin-2-ylidene and 1,3-bis(adamantyl)imidazolin-2-ylidene.

The process for preparing free heterocyclic carbenes of the imidazole type described in J. Am. Chem. Soc. 1991, 113, pp. 361–63 comprises reacting an imidazolium salt with a deprotonation reagent in a polar aprotic solvent at relatively high temperatures.

The deprotonation reagent used here is sodium hydride in the presence of catalytic amounts of dimethyl sulfoxide (DMSO) or potassium tert-butoxide; the polar aprotic solvent used is tetrahydrofuran (THF).

The work-up of a free carbene prepared in this way is usually carried out by filtering off the precipitated salts, removing the solvent under reduced pressure and distilling or subliming the residue containing the carbene in a high vacuum at relatively high temperatures. This procedure has the disadvantage that the frequently temperature-sensitive free carbenes are subjected during the purification to a thermal stress which leads to the formation of downstream products and thus to losses in yield. In addition, for reasons of solubility and/or volatility, only a very small selection of carbenes is obtainable in good yield and in pure form, in particular in the case of oily imidazolium salts and their carbene products. A further disadvantage is that in the known procedure the deprotonation rate using the customary reagents and solvents is low, in particular at the relatively low temperatures which are desirable for the stability of the carbenes formed. If the higher temperatures actually required for the deprotonation are employed, the carbenes formed decompose completely or partially even at room temperature. This is compounded by the fact that most polar aprotic solvents such as DMSO or acetonitrile can only be obtained in anhydrous form with a considerable outlay in terms of apparatus and money. In addition, restrictions are placed on the solvents used in terms of their acidity; thus, nitromethane is unsuitable as solvent because of its relatively high acidity, although it has good solvent properties for the azolium salts.

The comparatively high boiling points of most polar aprotic solvents (e.g. 189° C. for DMSO) are also disadvantageous in that the individual reaction components cannot be separated completely from one another. This likewise leads to a reduction in yield and to the formation of impure products. This procedure is particularly disadvantageous if downstream products of metal complexes are to be prepared in good yields, i.e. the free carbene is to be prepared from the imidazolium salt and reacted in a single-vessel process with metal-containing components (e.g. metal halides and acetylacetonates) to give metal-carbene complexes.

It is therefore an object of the invention to provide a generally useable process for preparing free heterocyclic carbenes which avoids the many disadvantages mentioned for known processes and makes it possible to prepare the carbenes in a simple manner at a high conversion and in a high selectivity.

This object is achieved by a process for preparing heterocyclic carbenes of the formula I

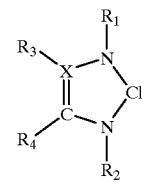

where $R^1$, $R^2$, $R^3$ and $R^4$ are identical or different and are saturated or unsaturated, straight-chain, branched or cyclic, unsubstituted or substituted $C_1$–$C_{10}$-alkyl, $C_2$–$C_5$-alkylidene, $C_2$–$C_5$-alkylidyne, $C_7$–$C_{19}$-aralkyl or $C_6$–$C_{14}$-aryl radicals, $R^3$ and $R^4$ can also be hydrogen or together form fused-on, substituted or unsubstituted radicals having 3–7 carbon atoms, X is carbon or nitrogen, with $R^3$ not being present when X is nitrogen, by reacting azolium salts of the formula II

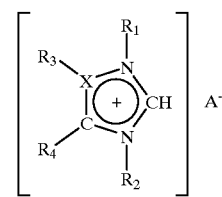

where $R^1$, $R^2$, $R^3$ and $R^4$ are as defined for the formula I and $A^-$ is a halide, pseudohalide, borate, phosphate, carboxylate or metal complex ion, with a deprotonation reagent in pure liquid ammonia or in pure organic amine or in a mixture of liquid ammonia or an organic amine and an organic polar aprotic solvent.

The process of the invention makes it possible to deprotonate azolium salts of the formula II under surprisingly mild reaction conditions. The reaction temperature is in the range from −75 to 0° C., preferably in the range from −50 to −20° C. and in particular from −50 to −30° C. It is here of decisive importance that the solvent used for the reaction is pure liquid ammonia or a pure organic amine or a mixture of liquid ammonia or an organic amine and an organic polar aprotic solvent. If pure liquid ammonia is used, the reaction temperature is from −75 to −35° C.

Organic polar aprotic solvents which can be used are, for example, tetrahydrofuran, dimethyl sulfoxide or acetonitrile, with the volume ratio of ammonia or organic amine to the polar aprotic solvent being from 1:0.01 to 1:100, preferably from 1:0.1 to 1:10 and in particular 1:0.2. Organic amines which can be used are primary $C_1$–$C_4$-alkylamines which are liquid at the reaction temperature, in particular methylamine or ethylamine.

Deprotonation reagents used are strong bases such as metal hydrides, metal amides, metal alkoxides, metal carboxylates, carbonylmetallates or hydrido(carbonyl) metallates. Preference is given to using alkali metal hydrides such as sodium hydride or alkali metal amides such as potassium amide. Based on the azolium salt of the formula II to be deprotonated, the deprotonation reagent is used in at least the stoichiometric amount, preferably in a 10% molar excess.

The reaction of the azolium salts of the formula II with the deprotonation reagent is carried out under strict exclusion of air and moisture by addition of the deprotonation reagent to the solution of the azolium salt in pure ammonia, in pure organic amine or in a mixture of ammonia or an organic amine and the organic polar aprotic solvent. The reaction proceeds at a high rate and is often essentially complete after a few minutes. However, to complete the reaction, it is advisable to adhere to reaction times of up to one hour. The reaction mixture obtained is first filtered to remove the precipitated metal salts. The filtered solution of the free carbene can be used without further work-up for downstream reactions, for example metal complex formation. When carrying out the deprotonation in a mixture of ammonia or an organic amine and a polar aprotic solvent, the ammonia or the organic amine may, if desired, be removed by evaporation before further processing of the carbene. In addition, any metal salts still present in small amounts are subsequently removed completely by filtration or decantation, advantageously with lowering of the temperature.

If the free carbene is to be isolated as a pure substance, i.e. free of solvent, the polar aprotic solvent and/or the organic amine is removed under reduced pressure. This is possible in a gentle manner at relatively low temperatures because the solvents used according to the process of the invention have relatively low boiling points.

If the deprotonation is carried out in pure ammonia, this can easily be completely removed from the reaction system either by increasing the temperature above the boiling point or at very low temperatures in the range from −50 to −100° C. by reducing the pressure, if desired by the technique of vacuum freeze drying.

Liquid ammonia has the advantage that it is miscible in all proportions with many organic solvents, it has a high solvent capability for organic salts, aromatic compounds and polar functional groups and is proton-inactive. The azolium salts used as starting materials dissolve better in pure ammonia and in mixtures of ammonia and a polar aprotic solvent than in the organic polar aprotic solvent itself.

A further advantage of liquid ammonia or its solutions with organic polar aprotic solvents is that freedom from water can be achieved in a simple manner, which is of particular importance for the stability of the resulting carbenes. Surprisingly, the heterocyclic carbenes prepared according to the process of the present invention are inert toward ammonia.

In addition, ammonia is a particularly inexpensive and nonhazardous solvent which does not absolutely have to be recycled.

The process of the invention can be applied to many azolium salts having the formula II where $R^1$, $R^2$, $R^3$ and $R^4$ are identical or different and are saturated or unsaturated, straight-chain, branched or cyclic, unsubstituted or substituted $C_1$–$C_{10}$-, preferably $C_1$–$C_6$-alkyl, $C_2$–$C_5$-, preferably $C_2$–$C_4$-alkylidyne, $C_2$–$C_5$-, preferably $C_2$–$C_4$-alkylidyne, $C_7$–$C_{19}$-, preferably $C_7$–$C_{10}$-aralkyl or $C_6$–$C_{14}$-aryl radical, preferably a phenyl radical, $R^3$ and $R^4$ can also be hydrogen or together form fused-on substituted or unsubstituted radicals having 3–7, preferably 4, carbon atoms, X is carbon or nitrogen, with $R^3$ not being present when X is nitrogen.

The radicals $R^1$, $R^2$, $R^3$ and $R^4$ can each bear one or more substituents such as amine, nitro, nitrile, isonitrile, ether, alcohol, aldehyde or ketone groups, carboxylic acid derivatives, in particular esters or amides, halogenated, in particular fluorinated or perfluorinated, hydrocarbon radicals, carbohydrate, phosphine, phosphine oxide, phosphine sulfide, phosphole radicals, phosphite derivatives, aliphatic or aromatic sulfonic acid derivatives, their salts, esters or amides, silyl functions, boryl groups or heterocyclic substituents. Preferably, one of the two radicals $R^1$ or $R^2$ has a heterocyclic substituent such as a pyridine ring or azolium salts.

The anion $A^-$ in the formula II is preferably a tetraphenylborate, tetrafluoroborate, hexafluorophosphate, acetate, tetracarbonylcobaltate, hexafluoroferrate (III), tetrachloroferrate(III), tetrachloroaluminate or tetrachloropalladate(II) ion.

The process of the invention makes it possible to prepare many previously unknown free carbenes in high yield and purity in very short reaction times. This is attributable, on the one hand, to the great structural variety of available azolium salts of the formula II and, on the other hand, to the mild and efficient deprotonation conditions which are surprisingly made possible by the solvents used. The process of the invention has therefore been found to be particularly useful for preparing thermally sensitive carbenes. Chiral and immobilized carbenes are also obtainable for the first time in this way. Owing to the simple reaction procedure, the process is also suitable for industrial use.

In view of the fact that the heterocyclic carbenes of the formula I are water-sensitive and ammonia has water-like properties, it is surprising to a person skilled in the art that the free heterocyclic carbenes are completely stable toward ammonia and that such high deprotonation rates have been found for the azolium salts of the formula II.

EXAMPLES

General Example for the preparation of 1,3-disubstituted imidazolin-2-ylidenes according to the following equation

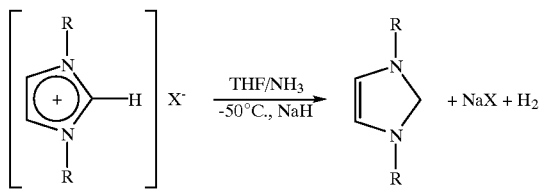

The apparatus for preparing the temperature-, air- and moisture-sensitive imidazolin-2-ylidenes comprises a condensation vessel fitted with gas inlet tube and overpressure valve for drying and purifying the ammonia plus a graduated reaction vessel which is equipped with a dry ice condenser and further devices for adding or taking out solvents, solutions and solids. The condensation vessel and the actual reaction vessel are connected to one another via a condensation bridge having two taps or another vacuum-resistant line.

The reaction vessel is charged under strict exclusion of air and moisture with 10 mmol of an azolium salt in 15 ml of a polar aprotic solvent such as THF. At about −70° C., 75 ml of ammonia (purity 99.8%) are condensed under reduced pressure into the condensation vessel which contains about 2 g of potassium, forming a deep blue solution.

Subsequently, the ammonia is condensed under reduced pressure via the condensation bridge into the actual reaction vessel. This vessel contains the suspension of the imidazolium salt to be deprotonated in THF. For this purpose, the condensation vessel is warmed gently while the reaction vessel and the dry ice condenser are cooled to about −70° C. by means of dry ice/acetone. The pressure in the apparatus is then equilibrated using inert gas.

11 mmol of the deprotonation reagent NaH are then added under an inert gas atmosphere and the cooling under the reaction vessel is removed. Granulated NaH is advantageously used. A clear colorless, occasionally somewhat yellowish solution is formed within one hour. After the reaction is complete, the ammonia is allowed to vaporize at atmospheric pressure or it is condensed under reduced pressure into the condensation vessel or into cold traps. After the ammonia has been removed completely from the reaction vessel, the resulting THF solution of the heterocyclic carbene is, to remove the sodium halide formed, made up with THF or toluene to a total volume of 30 ml and filtered. The carbene solutions thus produced are spectroscopically pure and can be employed without further purification in downstream reactions.

In the following examples, the preparation of the corresponding imidazolium salts is described first. The free carbenes are produced therefrom according to the above equation. The free carbenes are characterized by reacting them with suitable transition metal precursors to give transition metal-carbene complexes and/or by $^1$H- and $^{13}$C-NMR spectroscopy of the free carbenes and of the oxidation products after reacting the free carbenes with elemental sulfur.

Example 1

1,3-dimethylimidazolin-2-yliden (1)

A) Preparation of 1,3-dimethylimidazolium diiodide (1a)

21.3 ml (267 mmol) of N-methylimidazole are dissolved in 150 ml of isopropanol. After addition of 17.3 ml (280 mmol) of methyl iodide, the mixture is heated at the boiling point for 8 hours. After cooling, the solution is allowed to stand for 12 hours to crystallize. The crystalline 1,3-dimethylimidazolium iodide (1a) is filtered off and washed with 50 ml of diethyl ether and 50 ml of THF. Yield: 57 g (96%).

$^1$H-NMR (400 MHz, CDCl$_3$, δ in ppm): 8.97 (s, NC$\underline{H}$N); 7.10 (s, NC$\underline{H}_2$C$\underline{H}_2$N); 3.46 (s, C$\underline{H}_3$); $^{13}$C-NMR (100.6 MHz, CDCl$_3$, ppm): 134.7 (s, NC$\underline{H}$N); 121.85 (s, N$\underline{C}$H$_2$$\underline{C}$H$_2$N); 35.29 (s, $\underline{C}$H$_3$).

B) Preparation of 1,3-dimethylimidazolin-2-ylidene (1)

10 mmol of 1,3-dimethylimidazolium iodide (1a) are deprotonated in 75 ml of NH$_{3(liq)}$/15 ml of THF by means of 11 mmol of NaH as described in the general example. Removing the ammonia under reduced pressure gives a colorless spectroscopically pure solution of 1,3-dimethylimidazolin-2-ylidene (1) in THF which is, to remove the sodium iodide, made up with toluene to a total volume of 40 ml and subsequently filtered. The filtrate is used without further purification for the synthesis of the complex.

$^{13}$C-NMR (100 MHz, THF, d$_8$-THF external reference, δ in ppm): 215.1 (s, N$\underline{C}$N): 120.6 (s, N$\underline{C}$H$_2$$\underline{C}$H$_2$N); 36.2 (s, $\underline{C}$H$_3$);

C) Preparation of chloro(η$^4$-1,5-cyclooctadiene)(1,3-dimethylimidazolin-2-ylidene)rhodim (I)

247 mg (0.5 mmol) of bis[(μ-chloro)(77$^4$−1,5-cyclooctadiene)rhodium] are dissolved at room temperature in 20 ml of absolute THF and admixed with 192 mg (1 mmol) of 1,3-dimethylimidazolin-2-ylidene. The mixture is stirred for a further 15 minutes at room temperature, the solvent is removed under reduced pressure and the residue is purified by washing with 10 ml of diethyl ether. Yield: 310 mg (91%).

Elemental analysis (C$_{13}$H$_{20}$ClN$_2$Rh) (in % by weight): calculated: C 45.57 H 5.88 N 8.17 found: C 45.63 H 5.98 N 8.35.

$^1$H-NMR (400 MHz, CDCl$_3$, 20° C., δ in ppm): 6.8 (s, 2H, C$\underline{H}$C$\underline{H}$); 4.1 (s, 6H, NC$\underline{H}_3$), 5.0 (2H); 3.3 (2H); 2.4 (4H); 1.9 (4H) (cyclooctadiene);

$^{13}$C{$^1$H}-NMR (100 MHz, CDCl$_3$, δ in ppm): 182.6 (d, N$\underline{C}$N, $^1$J(C—Rh)=50 Hz); 121.9 ($\underline{C}$H$_2$$\underline{C}$H$_2$); 37.6 (N$\underline{C}$H$_3$); 98.5; 67.7; 33.0; 28.9 (cyclooctadiene).

Example 2

1,1'-(1,2-ethylene)-3,3'-dimethyldiimidazolin-2,2'-diylidene (2)

A) Preparation of 1,1'-(1,2-ethylene)-3,3'-dimethyldiimidazolium dibromide (2a)

5 ml (58 mmol) of 1,2-dibromethane, 9.25 ml (116 mmol) of N-methylimidazole and 10 ml of methanol as solvent are heated at a temperature of 80° C. for two hours. After cooling, the solvent is removed under reduced pressure. This gives 18.5 g (92%) of a white solid which represents the desired product (2a).

$^1$H-NMR (400 MHz, CDCl$_3$, δ in ppm): 9.29 (NC$\underline{H}$N); 7.77 (C$\underline{H}$C$\underline{H}$), 4.77 (NC$\underline{H}_2$C$\underline{H}_2$N); 3.85 (NCH$_3$);

$^{13}$C-NMR (100 MHz, CDCl$_3$, δ in ppm): 137.1 (N$\underline{C}$HN); 123.7; 122.8 ($\underline{C}$H$\underline{C}$H); 48.2 (N$\underline{C}$H$_2$$\underline{C}$H$_2$N); 36.0 (N$\underline{C}$H$_3$).

B) Preparation of 1,1'-(1,2-ethylene)-3,3'-dimethyldiimidazolin-2,2'-diylidene (2).

10 mmol of the diimidazolium salt (2a) are deprotonated using 22 mmol of NaH in NH$_3$/THF in a volume ratio of 5:1 as described in the general example. Removing the ammonia gives a spectroscopically pure solution of the dicarbene in THF.

$^{13}$C-NMR (100 MHz, THF, 10° C., δ in ppm): 215.9 (N<u>C</u>N); 120.3; 119.7 (N<u>C</u>H<u>C</u>HN); 52.7 (<u>C</u>H$_2$N); 37.7 (N<u>C</u>H$_3$).

C) Preparation of [1,1'-(1,2-ethylene)-3,3'-dimethyldiimidazolin-2,2'-diylidene]bis[chloro(η$^4$-1,5-cyclooctadiene)rhodium(I)]

247 mg (0.5 mmol) of bis[(μ-chloro)(η$^4$-1,5-cyclooctadiene)rhodium] are dissolved at room temperature in 20 ml of absolute THF and admixed with 190 mg (1 mmol) of 1,1'-(1,2-ethylene)-3,3'-dimethyldiimidazolin-2,2'-diylidene (2). The mixture is stirred for 3 hours at room temperature, the solvent is removed under reduced pressure and the product is purified by washing with 10 ml of diethyl ether. The product is dissolved in 10 ml of methylene chloride and covered with a layer of 20 ml of pentane. The solvent mixture is decanted from the resulting crystals and the crystals are dried under reduced pressure. The pale yellow crystals are readily soluble in chloroform and methylene chloride. Yield: 80 mg (18%).

$^1$H-NMR (400 MHz, CDCl$_3$, 20° C., δ in ppm): 6.85 (d, 2H, J=1.9 Hz), 6.47 (d, 2H, J=1.9 Hz, N<u>C</u>H), 4.01 (s, 6H, NC<u>H</u>$_3$), 4.73 (m, 4H, C<u>H</u>$_2$C<u>H</u>$_2$); 3.34 (m, 4H); 3.22 (m, 4H); 2.44 (m, 4H); 2.00 (m, 4H), 5.17 (m, 4H); 4.98 (m, 4H, cyclooctadiene).

$^{13}$C-NMR (100 MHz, CDCl$_3$, 20° C., δ in ppm: 181.3 (d, $^1$J$_{C-Rh}$=50.5 Hz, N<u>C</u>N); 123.9; 120.6 (N<u>C</u>H); 37.8 (N<u>C</u>H$_3$); 50.9 (<u>C</u>H$_2$<u>C</u>H$_2$), 69.2 (d, $^1$J$_{C-Rh}$=14.6 Hz), 67.8 (d, $^1$J$_{C-Rh}$=14.5 Hz); 29.5; 28.4 (cyclooctadiene);

Elemental analysis (C$_{26}$H$_{28}$Cl$_2$N$_4$Rh$_2$*CH$_2$Cl$_2$) (in % by weight): Calculated: C 42.21 H 5.25 N 7.29 Found: C 43.02 H 5.41 N 7.31.

Example 3

N,N'-1,3-Di(n-hexyl)imidazolin-2-ylidene (3)

A) Preparation of N,N'-1,3-di(n-hexyl)imidazolium bromide (3a)

1st stage: Preparation of the potassium imidazolide C$_3$H$_3$N$_2$K 4 g (100 mmol) of potassium are added to 100 ml of toluene and heated at 80–100° C. until the potassium has melted to form small spheres. The mixture is cooled slowly to about 40° C., 7.5 g (110 mmol) of imidazole are added a little at a time and the mixture is heated again. A white precipitate forms and gas is evolved. When the addition of the imidazole has been completed, the mixture is heated for 2 hours at boiling point and is allowed to cool. The white precipitate is filtered off and dried. Yield: 10.3 g (97%).

$^1$H-NMR (400 MHz, 25° C., CDCl$_3$, δ in ppm): 7.72 (s,1), 7.02 (s,2).

2nd Stage: Preparation of monoalkylated N-(n-hexyl) imidazole 4 g (37 mmol) of potassium imidazolide are suspended in 100 ml of toluene. 6.0 ml (42 mmol) of 1-bromohexane are added, the mixture is heated while stirring to 110° C., this temperature is maintained for 5 hours and the mixture is then cooled slowly. The potassium bromide formed is filtered off and the toluene is partially removed under reduced pressure. The product remains in the form of a clear, slightly yellowish liquid. Yield: 5.2 g (93%).

$^1$H-NMR (400 MHz, 25° C., CDCl$_3$, δ in ppm): 7.91(d,2), 7.83(s,1), 3.79(t,2), 1.86(m,2), 1.82(m,2), 1.65(m,2), 1.53 (m,2), 1.48(m,3).

3rd Stage: Preparation of the dialkylated N,N'-(1,3-di(n-hexyl)imidazolium bromide (3a)

5.2 g (34 mmol) of N-(n-hexyl)imidazole are dissolved in 100 ml of toluene and admixed with a further 5.6 ml of 1-n-hexyl bromide. The mixture is heated while stirring for 3 hours at 110° C. and is then allowed to cool. The oily product is produced with formation of a second phase. The toluene is removed under reduced pressure. Yield: 10.0 g (92%).

$^1$H-NMR (400 MHz, 25° C., C$_6$D$_6$, δ in ppm): 9.24(s,1), 7.52(s,2), 4.23(t,4), 1.90(m,4), 1.35(m,12), 0.9(m,6).

$^{13}$C-NMR (100 MHz, 25° C., C$_6$D$_6$, δ in ppm): 137.50, 123.27, 50.42, 31.70, 30.48, 26.31, 23.06, 14.16.

B) Preparation of N,N'-1,3-di(n-hexyl)imidazolin-2-ylidene (3)

The preparation is carried out as described in the general example and gives a spectroscopically pure solution of 10 mmol of N,N'-1,3-di(n-hexyl)imidazolin-2-ylidene in 40 ml of THF.

C) Preparation of pentacarbonyl[1,3-di-(n-hexyl) imidazolin-2-ylidene)tungsten 3 mmol of a carbene solution of di-n-hexylcarbene (set free as described in the general example from the salt N,N'-(1,3-di(n-hexyl)imidazolium bromide prepared under Point A)) are added to a solution of 1 g (2.8 mmol) of hexylcarbonyltungsten in 50 ml of THF. A yellow solid is formed. Yield: 1.31 g (82%).

$^{13}$C-NMR (100 MHz, 25° C., C$_6$D$_6$, δ in ppm): 198.69, 122.37, 53.22, 31.50, 30.85, 27.61, 23.05, 14.18.

D) Preparation of 1,3-di(n-hexyl)imidazoline-2-thione

A carbene solution of di-n-hexyl carbene (set free by the ammonia route from the salt N,N'-(1,3-di(n-hexyl) imidazolium bromide prepared under Point 2) is added to a solution of 0.2 g (5.5 mmol) of flowers of sulfur. A yellow solid precipitates. Yield: 1.40 g (95%).

$^{13}$C-NMR (100 MHz, 25° C., CDCl$_3$, δ in ppm): 189.65, 124.21, 52.67, 36.29, 34.03, 31.17, 27.65, 19.12.

Example 4

N,N'-1,3-Di(1H,1H,2H,2H-tridecafluorooctyl) imidazole-2-ylidene (4)

A) Preparation of N,N'-1,3-di(1H,1H,2H,2H-tridecafluorooctyl)imidazolium iodide (4a)

Preparation of the monoperfluoroalkylated ligand precursor N-(1H,1H,2H,2H-tridecafluorooctyl)imidazole 2 g (18.5 mmol) of potassium imidazolide (cf. Example 3A) are suspended in 100 ml of toluene. 5.2 ml (21 mmol) of 1H,1H,2H,2H-tridecafluorooctyl iodide are added, the mixture is heated while stirring for 16 hours at 110° C. and then cooled slowly. The potassium iodide formed is filtered off and the toluene is removed under reduced pressure. This leaves the product in the form of a clear, slightly yellowish liquid. Yield: 6.0 g (79%).

$^1$H-NMR (400 MHz, 25° C., CDCl$_3$ δ in ppm): 7.86(s,1), 7.67(s,1), 7.09(s,1), 4.42(t,2), 2.72(n,2).

$^{13}$C-NMR (100 MHz, 25° C., C$_6$D$_6$, δ in ppm): 135.07, 121.27, 118.59, 46.42, 38.78, 36.82, 36.61, 35.85, 33.01, 32.73, 32.19.

Preparation of the doubly perfluoroalkylated N,N'-1,3-di (1H,1H,2H,2H-tridecylfluorooctyl)imidazolium iodide 6.0 g (14 mmol) of N-(1H,1H,2H,2H-tridecafluorooctyl) imidazole are dissolved in 100 ml of toluene and admixed with a further 3.6 ml (15 mmol) of 1H,1H,2H,2H-tridecafluorooctyl iodide. The mixture is then heated while stirring for 12 hours at 110° C. and then allowed to cool. The toluene is removed under reduced pressure. The resulting product is a viscous resin. Yield: 9.6 g (78%).

$^1$H-NMR (400 MHz, 25° C., C$_6$D$_6$, δ in ppm): 9.24(s,1), 7.52(s,2), 4.74(t,4), 2.91(m,4).

$^{13}$C-NMR (100 MHz, 25° C., CDCl$_3$, δ in ppm): 138.4, 119.2, 47.5, 39.7, 35.0, 36.8, 36.3, 35.6, 34.1, 32.7, 32.4.

B) Preparation of N,N'-1,3-di(1H,1H,2H,2H-tridecafluorooctyl)imidazolin-2-ylidene (4)

The preparation is carried out from (4a) as described in the general example and gives a solution of 10 mmol of the free, spectroscopically pure carbene (4) in 40 ml of THF.

$^{13}$C-NMR (100 MHz, 25° C., THF, δ in ppm): 214.5, 117.5, 67.5, 59.0, 36.9, 36.2, 35.7, 34.2, 32.7, 32.5.

Example 5

1,3-Dicyclohexylimidazolin-2-ylidene (5)

A) Preparation of 1,3-dicyclohexylimidazolium chloride (5a)

A 500 ml round-bottom flask is charged with 9.92 g (100 mmol) of cyclohexylamine in 100 ml of toluene. 30 g (100 mmol) of paraformaldehyde are added while stirring vigorously. After 30 minutes at room temperature, the flask is cooled to 0° C. using an ice bath and a further 9.92 g (100 mmol) of cyclohexylamine are added. While cooling and stirring vigorously, 30 ml (100 mmol) of a 3.3 molar HCl solution are then slowly added dropwise. The cooling is then removed, 145 ml (100 mmol) of 40% strength aqueous glyoxal solution are slowly added and the reaction mixture is stirred overnight at 50° C.

For the work-up, 100 ml of ether and 50 ml of saturated sodium carbonate solution are added. If necessary, the emulsion which forms is broken by addition of a little pentane. The ether phase is separated off, the aqueous phase is washed three times with 100 ml each time of ether and the volatile constituents are removed under reduced pressure. The residue is extracted with 150 ml of dichloromethane, dried over MgSO$_4$ and filtered.

Removal of the solvent under reduced pressure leaves a bulky foam which is washed with ether and can then be broken up to give a white hygroscopic powder. Yield 23.5 g (75%).

$^1$H-NMR (400 MHz, 25° C., CDCl$_3$, δ in ppm): 10.43 (s, 1H, N$_2$C—H), 7.41 (m, 2H, C—H), 4.33 (m, 1H, R$_3$C—H), 1.0–2.0 (overlapping multiplets, 20H, cyclohexyl-CH$_2$).

$^{13}$C-NMR (100 MHz, CDCl$_3$, δ in ppm): 134.9 (N$_2$C—H), 119.7 (C—H), 59.3 (H—CR$_3$), 33.1 (CH—$\underline{C}$H$_2$), 24.5 (2CH$_2$), 24.2 (CH$_2$).

Mass spectrum (FAB): m/e=501.4 ([ME$^+$+M−Cl], 6.4), 233 ([M$^+$−Cl], 100).

B) Preparation of 1,3-dicyclohexylimidazolin-2-ylidene (5)

2.68 g (10 mmol) of 1,3-dicyclohexylimidazolium chloride (5a) are deprotonated in accordance with the general description in a mixture of 20 ml of THF and 100 ml of NH$_3$ using 260 mg (10.8 mmol) of NaH. A virtually colorless solution of 1,3-dicyclohexylimidazolin-2-ylidene (5) is formed. After removing the ammonia, the mixture is made up with THF to 40 ml and the solution thus obtained is used further without further work-up.

$^{13}$C-NMR (100 MHz, THF, CD$_3$NO, δ in ppm): 210.1 (C:), 115.7 (C=C), 66.8 (N—CH), 59.6 (2CH$_2$), 34.9 (2CH$_2$) 25.9 (CH$_2$).

C) Preparation of pentacarbonyl(1,3-dicyclohexylimidazolin-2-ylidene)tungsten (5b)

A Schlenk tube is charged with 880 mg (2.5 mmol) of hexacarbonyltungsten in 100 ml degassed THF. While stirring 10 ml (2.5 mmol) of 0.25 M carbene solution (5) are then added dropwise under a protective gas atmosphere and the reaction mixture is stirred for a few hours. The solvent is then removed under reduced pressure and any hexycarbonyltungsten still present is sublimed off overnight at room temperature.

The residue is dissolved in methylene chloride and filtered. After concentrating the mother liquor, the product (5b) can be obtained by slow cooling in the form of yellow crystals. Yield: 854 mg (61%).

$^1$H-NMR (400 MHz, CDCl$_3$ δ in ppm): 7.00 (s, 2H, N—CH=), 4.75 (m, 2H, N—CH), 1.98 (m, 4H, CH$_2$), 1.87 (m, 4H, CH$_2$ ), 1.75 (m, 2H, CH$_2$), 1.45 (m, 8H, CH$_2$), 1.24 (m, 2E, CH$_2$).

$^{13}$C-NMR (100 MHz, CDCl$_3$, δ in ppm): 201.5 (J($^{183}$W—$^{13}$C)=126 Hz, W—CO), 197.7 (J($^{183}$W—$^{13}$C)=126 Hz, W—(CO)$_4$), 176.4 (J($^{183}$W—$^{13}$C)=99 Hz, W—CN$_2$), 118.34 (C=C), 61.7 (N—CH), 34.4 (CH-$\underline{C}$H$_2$), 25.5 (CH$_2$), 25.1 (CH$_2$(C$_2$H$_4$)$_2$).

Mass spectrum (CI): m/e=556 ([M$^+$, 22), 528 ([M$^+$−CO], 6), 233 ([M$^+$−W(CO$_5$)], 100).

Elemental analysis (in % by weight): Calculated: C 43.18 H 4.3 N 5.0 Found: C 43.17 H 4.46 N 5.04.

D) Preparation of chloro(η$^4$-5-cyclooctadiene)(1,3-dicyclohexylimidazolin-2-ylidene)rhodium (5c)

A Schlenk tube is charged with 200 mg (0.4 mmol) of bis[(μ-chloro)(η$^4$-1,5-cyclooctadiene)rhodium] in 5 ml of THF. 3.3 ml (0.8 mmol) of carbene solution (5) are slowly added to this solution.

The reaction mixture is stirred further for one hour at room temperature, the solvent is then taken off, the residue is taken up in methylene chloride and filtered. The complex is precipitated by addition of pentane and subsequently washed with pentane. Removal of the volatile constituents under reduced pressure gives the complex as a yellow powder. Yield: 325 mg (85%).

$^1$H-NMR (400 MHz, CDCl$_3$, δ in ppm): 6.78 (s, 2H, NCH=), 5.27 (m, 2H, COD—CH), 4.93 (m, 2H, N—CH), 3.23 (m, 2H, COD—CH), 2.31 (m, 4H, COD—CH$_2$), 1.89 (m, 4H, COD—CH), 1.91–1.15 (overlapping multiplets, 22H, cyclohexyl-CH$_2$).

$^{13}$C-NMR (100 MHz, CDCl$_3$, δ in ppm): 180.1 (d, J(Rh—$^{13}$C)=51 Hz), Rh—CN$_2$), 117.5 (N—CH=), 97.8 (d, J(Rh—$^{13}$C)=3 Hz), COD—CH), 97.7 (d, J(Rh—$^{13}$C)=3 Hz), COD—CH), 67.5 (d, J(Rh—$^{13}$C)=14 Hz, COD—CH), 60.6 (N—CH), 34.5 (COD—CH$_2$), 34.4 (cyclohexyl-CH$_2$), 33.4 (cyclohexyl-CH$_2$), 29.2 (COD—CH$_2$), 26.4 (cyclohexyl-CH$_2$), 26.1 (cyclohexyl-CH$_2$), 25.7 (cyclohexyl-CH$_2$).

Example 6

1-Methyl-3-(2-phenylethyl)imidazolin-2-ylidene (6)

A) Preparation of 1-methyl-3-(2-phenylethyl)imidazolium chloride (6a)

5.0 ml (62.7 mmol) of N-methylimidazole are heated together with 8.23 ml (8.82 g; 62.7 mmol) of 1-chloro-2-phenylethane without addition of a solvent for 18 hours at 140° C. After cooling, the resulting 1-methyl-3-(2-phenylethyl)imidazolium chloride (6a) is allowed to stand to crystalize.

$^1$H-NMR (400 MHz, D$_2$O, δ in ppm): 8.23 (s, NC$\underline{H}$N); 7.0–7.2 (m, 5H, Ph); 6.9 (2H, NC$\underline{H}$C$\underline{H}$N); 4.32 (2H, NC$\underline{H}_2$), 3.6 (3H, NCH$_3$), 2.95 (2H, C$\underline{H}_2$Ph).

$^{13}$C-NMR (100 MHz, D$_2$O, ppm): 137.04 (s, N$\underline{C}$HN); 136.11; 135.96; 129.17; 129.00; 127.48; 123.75; 123.66 (Ph—$\underline{C}$); 122.43; 122.34 (N$\underline{C}$H$\underline{C}$HN); 50.91 (N$\underline{C}$H$_2$); 35.82 (s, $\underline{C}$H$_3$); 35.75 ($\underline{C}$H$_2$Ph).

B) Preparation of 1-methyl-3-(2-phenylethyl)imidazolin-2-ylidene (6)

As described in the general example, 10 mol of 1-methyl-3-(2-phenylethyl)imidazolium-chloride (6a) are deprotonated in a mixture of ammonia and THF by means of 11 mmol of NaH. Removal of the ammonia and filtration of the THF solution made up to 40 ml results in a clear, spectroscopically pure solution of 1-methyl-3-(2-phenylethyl) imidazolin-2-ylidene (6).

$^{13}$C-NMR (100 MHz, d$_8$-THF/THF external reference, δ in ppm): 214.2 (s, N$\underline{C}$N); 140.3; 130.0; 129.5; 126.4 (Ph—$\underline{C}$); 122.43; 122.34 (N$\underline{CH}$$\underline{CH}$N); 53.0 (N$\underline{CH}_2$); 39.2 (s, $\underline{C}H_3$); 37.8 ($\underline{C}H_2$Ph).

Example 7

1,2-Bis(2-ethoxyethyl)imidazolin-2-ylidene (7)

A) Preparation of 1-(2-ethoxyethyl)imidazole (7a)

A Schlenk tube is charged with 5.5 g (52 mmol) of potassium imidazolide in 50 ml of THF. While stirring, 7.7 g (50 mmol) of 2-bromoethyl ethyl ether are added and the suspension is stirred for 4 hours, then warmed gently. After cooling, the reaction mixture is filtered and the solvent is removed. Distillation in a high vacuum gives 7a as a colorless liquid. The purity was checked by GC-MS. Only one fraction was observed here.

Mass spectrum (GC-MS): m/e=140 ([M$^+$],80), 96 ([M$^+$−CH$_3$CH$_2$OCH$_2$+H],78), 81 ([M$^+$−CH$_3$CH$_2$OCH$_2$CH$_2$], 100), 59 (CH$_3$CH$_2$OCH$_2^+$, 75), 41 (85)

B) Preparation of 1,2-bis(2-ethoxyethyl)imidazolium chloride (7b)

7 g (45 mmol) of 2-bromoethyl ethyl ether are added to 4.5 g (39 mmol) of 1-(2-ethoxyethyl)imidazole in 50 ml of THF and the mixture is refluxed for 12 hours. A second liquid phase forms. After cooling to 0° C., the solvent is decanted off and the residue is extracted three times with THF. Removal of the solvent under reduced pressure gives (7b) (7.2 g, 75%) as a yellowish oil.

$^1$H-NMR (400 MHz, 25° C., CDCl$_3$ δ in ppm): 9.91 (s, 1H, N$_2$C—H), 7.53 (d, J=1 Hz, 2H, CH), 4.50 (t, J=5 Hz, 4H, N—CH$_2$), 3.74 (t, J=5 Hz, 2H, NCH$_2$$\underline{C}H_2$), 3.44 (q, J=7 Hz, 4H, O—CH$_2$), 1.08 (t, J=7 Hz, CH$_3$).

$^{13}$C-NMR (100 MHz, CDCl$_3$, δ in ppm): 136.5 (N$_2$C—H), 122.5 (NC—H), 67.9 (N—CH$_2$), 66.4 (NCH$_2$—$\underline{C}H_2$), 49.8 (O—CH$_2$), 14/7 (CH$_3$).

Mass spectrum (FAB): m/e=505 ([M$^+$+M−Br], 2), 213) [M$^+$−Br], 100).

C) Preparation of 1,2-bis(2-ethoxyethyl)imidazolin-2-ylidene (7)

2.93 g (10 mmol) of 1,2-bis(2-ethoxyethyl)imidazolium chloride (7b) are deprotonated as described above in a mixture of 20 ml of THF and 100 ml of NH$_3$ using 260 mg (10.8 mmol) of NaH. Only after the addition of ammonia does the yellow oil dissolve completely. The reaction is complete after only 30 minutes. After evaporating the ammonia, the mixture is made up with THF to 40 ml and the resulting solution is used further without further work-up.

D) Preparation of 1,3-bis(2-ethoxyethyl)imidazoline-2-thione (7c)

In a Schlenk tube, 80 mg (2.5 mmol) of sulfur are suspended in 10 ml of degassed THF. While stirring, 10 ml (2.5 mmol) of 0.25 M carbene solution (7) are added dropwise and the reaction mixture is stirred for 1 hour. The solvent is removed under reduced pressure, the residue is dissolved in methylene chloride and filtered. After concentrating the mother liquor, the product can be obtained by slow cooling in the form of yellow crystals. Yield: 446 mg (84%).

$^1$H-NMR (400 MHz, CDCl$_3$ δ in ppm): 6.75 (s, 2H, N—CH=). 4.16 (t, J=5.5 Hz, 4H, N—CH$_2$), 3.63 (t, J=5.5 Hz, 4H, N—CH$_2$$\underline{C}H_2$), 3.39 (q, J=7 Hz, 4H, O—CH$_2$), 1.08 (t, J=7 Hz, 6H, CH$_3$).

$^{13}$C-NMR (100 MHz, CDCl$_3$, δ in ppm): 161.2 (C=S), 117.7 (N—CH=), 69.2 (N—CH$_2$), 66.3(NCH$_2$$\underline{C}H_2$), 47.7 (OCH$_2$), 14.9 (CH$_3$).

E) Preparation of pentacarbonyl[1,3-(2'-ethoxyethyl) imidazolin-2-ylidene]tungsten (7d)

A Schlenk tube is charged with 880 mg (2.5 mmol) of hexacarbonyltungsten in 10 ml of degassed THF. While stirring, 10 ml (2.5 mmol) of 0.25 M carbene solution (7) are then added dropwise under a protective gas atmosphere and the reaction mixture is stirred for a few hours. The solvent is then removed under reduced pressure and any hexacarbonyltungsten still present is sublimed off overnight at room temperature.

The residue is dissolved in methylene chloride and filtered. After concentrating the mother liquor, the product can be obtained by slow cooling in the form of yellow crystals. Yield: 1.01 g (75%).

$^1$H-NMR (400 MHz, CDCl$_3$ δ in ppm): 7.23 (NCH=), 4.38 (t, J=5 Hz, 4H, N—CH$_2$), 3.69 (t, J=5 Hz, 4H, N—CH$_2$—$\underline{C}H_2$), 3.49 (q, J=7 Hz, 4H, OCH$_2$), 1.17 (t, J=7 Hz, 6H, CH$_3$).

$^{13}$C-NMR (100 MHz, CDCl$_3$, δ in ppm): 200.7 (J($^{183}$W—$^{13}$C)=125 Hz, W—CO), 197.9 (J($^{183}$W—$^{13}$C)=125 Hz, W(CO)$_4$), 178.6 (W—CN$_2$), 122.2 (N—CH), 70.0 (N—CH$_2$), 66.8 (NCH$_2$—$\underline{C}H_2$), 52.7 (OCH$_2$), 15.0 (CH$_3$).

Mass spectrum (CI): m/e=536 ([M$^+$], 6), 508 ([M$^+$−CO], 12), 480 ([M$^+$−2CO], 6), 213 (M$^+$−W(CO)$_5$], 100).

Elemental analysis (in % by weight): Calculated: C 35.84 H 3.79 N 5.22 W 34.28 Found: C 35.86 H 3.86 N 5.29 W 34.04.

Example 8

1-(2'-Diethylaminoethyl)-3-methylimidazolin-2-ylidene (8)

A) Preparation of 1-(2'-diethylaminoethyl)-3-methylimidazolium chloride hydrochloride (8a)

4.9 g (60 mmol) of N-methylimidazole are added to 8.6 g (50 mmol) of 2-(diethylamino)ethyl chloride hydrochloride in 50 ml of absolute ethanol and the mixture is refluxed for 12 hours.

After the reaction is complete, the solvent is removed under reduced pressure and the residue is washed a number of times with THF. This gives the product (8a) as a white hygroscopic powder. Yield: 108 g (85%).

$^1$H-NMR (400 MHz, DMSO-d$_6$ δ in ppm): 9.56 (s, 1H, C—H), 8.05 (m, 1H, H—C=), 7.79 (m, 1H, =CH), 4.69 (t, J=6.5 Hz, 2H, N—CH$_2$), 3.84 (s, 3H, N—CH$_3$), 3.52 (t, 2H, J=6.5 Hz, 2H, CH$_2$), 3.08 (q, J=7 Hz, 4H, CH$_2$, 1.17 (t, J=7 Hz, 6H, CH$_3$).

$^{13}$C-NMR (100 MHz, DMSO-d$_6$, δ in ppm): 141.8 (C—H), 127.7 (H—C=), 126.4 (=C—H), 53.9 (imidazole CH$_2$), 50.7 (N—CH$_2$), 47.5 (imidazole-CH$_2$—$\underline{C}H_2$, 39.9 (imidazole-CH$_3$), 12.8 (CH$_3$).

Mass spectrum (FAB): m/e=399 ([M$^+$+M−2 HCl−Cl], 18), 182 ([M$^+$−HBr−Br], 100).

B) Preparation of 1-[(2-diethylamino)ethyl]-3-methylimidazolin-2-ylidene (8)

2.54 g (10 mmol) of 1-[(2-diethylamino)ethyl)-3-methylimidazolium chloride hydrochloride (8a) are suspended in 20 ml THF. 100 ml of ammonia are subsequently condensed into this. 21 mmol of NaH are added at −78° C. The colorless solution is stirred under reflux for about 1 hour until gas evolution ceases. After removing the ammonia, the mixture is made up with THF to 40 ml and the resulting 0.25 molar carbene solution is used further without further work-up.

$^{13}$C-NMR (100 MHz, THF/CD$_3$NO, δ in ppm): 210 (C:), 119.1 (H—C=), 118.5 (=C—H), 53.9 (CH$_2$), 49.2 (CH$_2$), 46.8 (CH$_2$), 37.5 (N—CH$_3$), 11.9 (CH$_3$).

c) Preparation of 1-(2'diethylaminoethyl)-3-methylimidazoline-2-thione (8b)

Using a method similar to the preparation of 1,3-bis(2-ethoxyethyl)imidazoline-2-thione (7c), 80 mg (2.5 mmol) of sulfur are admixed with 1-(2'-diethylaminoethyl)-3-methylimidazolin-2-ylidene solution (8). This gives (8b) (478 mg, 89% of theory) as a yellow oil.

$^1$H-NMR (400 MHz, CDCl$_3$ δ in ppm): 6.63 (d, J=2.5 Hz, 1H, H—C═), 6.49 (d, J=2.5 Hz, 1H, H—C—) 3.86 (t, J=6 Hz, 2H, imidazole-N—CH$_2$), 3.37 (s, 3H, N—CH$_3$), 2.53 (t, J=6 Hz, 2H, imidazole-N—CH$_2$C$\underline{H}_2$), 2.33 (q, J=7 Hz, 4H, N—CH$_2$), 0.76 (t, J=7 Hz, 6H, CH$_3$).

$^{13}$C-NMR (100 MHz, CDCl$_3$, δ in ppm): 161.4 (C═S), 117.3 (H—C═), 116.7 (H—C═), 51.0 (imidazole-N—CH$_2$), 46.9 (imidazole-N—CH$_2$C$\underline{H}_2$), 45.9 (N—CH$_2$), 34.5 (N—CH$_3$), 11.6 (CH$_3$).

Mass spectrum (GC-MS) m/e=213 ([M$^+$], 13), 141 ([M$^+$-NEt$_2$], 13), 113 ([M$^+$-C$_2$H$_4$NEt$_2$], 8), 99 ([M$^+$-NC$_2$H$_4$NEt$_2$], 100), 86 (99), 71 (59), 56 (41), 42 (31).

D) Preparation of chloro(η$^4$-1,5-cyclooctadiene)]1-(2-diethylaminoethyl)-3-methylimidazolin-2-ylidene]rhodium (8c)

200 mg (0.4 mmol) of bis[(μ-chloro)(η$^4$-1,5-cyclooctadiene)rhodium] are initially charged in 5 ml of THF and, while stirring, slowly admixed with 3.3 ml (0.8 mmol) of a freshly prepared solution of 1-(2-diethylaminoethyl)-3-methylimidazolin-2-ylidene (8). After 1 hour at room temperature, the solvent is removed under reduced pressure and the residue is taken up in dichloromethane and filtered.

Removal of the solvent under reduced pressure gives (8c) as a yellow oil. Yield: 281 mg (81%).

$^1$H-NMR (400 MHz, CDCl$_3$, δ in ppm): 6.93 (d, J=1.6 Hz, 1H, H—C═), 6.72 (d, J=1.6 Hz, 1H, ═C—H), 4.95 (m, 2H, COD—CH), 4.69 (m, 1H, imidazole-CH$_2$), 4.29 (m, 1H, imidazole-CH$_2$), 4.00 (s, 3H, N—CH$_3$), 3.29 (m, 1H, COD—CH), 3.18 (m, 1H, COD—CH), 2.97 (m, 1H, imidazole-CH$_2$—C$\underline{H}_2$), 2.75 (m, 1H, imidazole-CH$_2$—C$\underline{H}_2$), 2.60 (m, 4H, N—CH$_2$, 2.35 (m, 4H, COD—CH$_2$), 1.95 (m, 2H, COD—CH$_2$), 1.8 (m, 2H, COD—CH$_2$), 1.06 ("t", J=7 Hz, 6H, CH$_3$).

$^{13}$C-NMR (100 MHz, CDCl$_3$, δ in ppm): 182.2 (d, J(Rh—$^{13}$C)=49.5 Hz, C—Rh), 121.5 (H—C═), 121.2 (═C—H), 98.37 (COD—CH), 98.1 (COD—CH), 68.1 (COD—CH), 67.3 (COD—CH), 53.8 (imidazole-CH$_2$), 49.0 (imidazole-CH$_2$— C$\underline{H}_2$), 47.5 (N—CH$_2$), 37.5 (imidazole-CH$_3$), 33.3 (COD—CH$_2$), 32.4 (COD—CH$_2$), 29.1 (COD—CH$_2$), 28.3 (COD—CH$_2$), 12.0 (CH$_3$).

Example 9

1-(2'-ethylaminoethyl)-3-methylimidazolin-2-ylidene (9)

A) Preparation of 1-(2'-ethylaminoethyl)-3-methylimidazolium chloride hydrochloride (9a)

4.0 g (60 mmol) of N-methylimidazole are added to 7.7 g (50 mmol) of 2-ethylaminoethyl chloride hydrochloride in 50 ml of absolute ethanol and the mixture is stirred for 36 hours at not more than 40° C. If higher temperatures are used, elimination takes place and the 1-methylimidazolium chloride thus formed can be removed only with difficulty. After the reaction is complete, the solution is concentrated under reduced pressure and the product is precipitated with ether. Washing a number of times with THF gives the product as a white hygroscopic powder. Yield: 9.3 g (83%).

$^1$H-NMR (400 MHz, DMSO-d$_6$ δ in ppm): 9.31 (s, 1H, N$_2$C—H), 7.85 (m, 1H, N—CH), 7.71 (m, 1H, N—CH), 4.62 (t, J=6 Hz, 2H, imidazole-CH$_2$), 3.82 (s, 3H, N—CH$_3$), 3.38 (t, J=6 Hz, 2H, imidazoleCH$_2$—C$\underline{H}$), 2.91 (q, J=7 Hz, 2H, N—CH$_2$) 1.21 (t, J=7 Hz, 3H, CH$_3$).

$^{13}$C-NMR (100 MHz, DMSO-d$_6$ δ in ppm): 139.2 (N$_2$CH), 125.4 (N—CH), 124.1 (N—CH), 47.1 (imidazole-N—CH$_2$), 46.7 (N—CH$_2$CH$_2$), 43.8 (N—CH$_2$), 37.5 (N—CH$_3$), 12.4 (CH$_3$).

Mass spectrum (FAB): m/e=343 ([M$^+$+M-Cl -2HCl], 18), 154 ([M$^+$-Cl HCl], 100).

Elemental analysis (in % by weight): Calculated: C 42.48 H 7.16 N 18.66 Cl 31.49 Found: C 41.97 H 7.55 N 18.59 Cl 30.77.

B) Preparation of 1-(2-ethylaminoethyl)-3-methylimidazolin-2-ylidene (9)

2.26 g (10 mmol) of 1-(2-ethylaminoethyl)-3-methylimidazolium chloride hydrochloride are dissolved in 20 ml of acetonitrile. 100 ml of ammonia are condensed into this.

20 mmol of NaH are added at −78° C. Gas evolution commences immediately. The colorless solution is stirred for about 1 hour under reflux until gas evolution ceases. After removing the ammonia, the mixture is made up with acetonitrile to 40 ml and the resulting 0.25 molar carbene solution (9) is used further without further work-up.

$^{13}$C-NMR (100 MHz, CH$_3$CN/CD$_3$NO, δ in ppm): 210.5 (C:), 120.8 (CH═), 120.6 (CH═), 51.4 (imidazole-N—CH$_2$), 51.2 (imidazole-NCH$_2$—CH$_2$), 44.4 (N—CH$_3$), 37.9 (N—CH$_2$), 15.6 (CH$_3$).

C) Preparation of 1-(2-ethylaminoethyl)-3-methylimidazoline-2-thione (9b)

320 mg of sulfur are added to the reaction mixture and the reaction vessel is shaken well. After 1 hour, insoluble salts are filtered off and the solvent is removed under reduced pressure. This gives (9b) as a brown oil.

$^1$H-NMR (400 MHz, CDCl$_3$ δ in ppm): 6.72 (d, J=2.5 Hz, 1H, H—C═), 6.60 (d, J=2.5 Hz, 1H, H—C═) 4.07 (t, J=6 Hz, 2H, imidazole-N—CH$_2$), 3.50 (s, 3H, N—CH$_3$), 2.91 (t, J=6 Hz, 2H, imidazole-N—CH$_2$—C$\underline{H}_2$), 2.59 (q, J=7 Hz, 2H, N—CH$_2$), 2.30 (bis, 1H, NH), 0.99 (t, J=7 Hz, 3H, CH$_3$).

$^{13}$C-NMR (100 MHz, CDCl$_3$, δ in ppm): 162.0 (C═S), 117.4 (H═C—), 117.3 (H—C═), 47.7 (imidazole-N—CH$_2$), 47.6 (imidazole-N—CH$_2$C$\underline{H}_2$), 43.6 (N—CH$_2$), 34.9 (N—CH$_3$), 14.9 (CH$_3$).

Example 10

1,3-Di(S)-1'phenylethyl]imidazolin-2-ylidene (10)

A) Preparation of 1,3-di[(S)-1'-phenylethyl]imidazolium chloride (10a)

11.9 g (100 mmol) of (S) −1-phenylethylamine are initially charged in 100 ml of toluene. While stirring vigorously, 3.0 g (100 mmol) of paraformaldehyde are added. Warming of the reaction mixture is prevented by means of a water bath. After 30 minutes at room temperature, the flask is cooled to 0° C. using an ice bath and a further 11.9 g (100 mmol) of (S)-1-phenylethylamine are added. While cooling and stirring vigorously, 30 ml (100 mmol) of a 3.3 molar HCl solution are slowly added dropwise. The cooling is then removed, 145 ml (100 mmol) of 40% strength aqueous glyoxal solution are slowly added and the reaction mixture is stirred overnight at 35–40° C.

For the work-up, 100 ml of ether and 50 ml of saturated sodium carbonate solution are added. If necessary, the emulsion which forms is broken by addition of a little pentane. The ether phase is separated off, the aqueous phase is washed three times with 100 ml each time of ether and dried under reduced pressure. The residue is taken up in 150 ml of dichloromethane, dried over MgSO$_4$ and filtered.

Removing the solvent under reduced pressure leaves a yellow oil which is washed a number of times with diethyl ether. This gives the product 10a as a slightly yellowish, very hygroscopic powder. Yield: 24.5 g (79%). The NMR spectra display only one set of signals, hence it can be concluded that isomerization does not take place.

$^1$H-NMR (400 MHz, CDCl$_3$ δ in ppm): 11.02 (s, 1H, N$_2$C—H), 7.37 (m, 2H, phenyl-CH), 7.28(s, 2H, N—CH), 7.21 (m, 3H, phenyl CH), 5.52 (q, J=7 Hz, 2H, R$_3$C—H), 1.88 (d, J=7 Hz, 6H, CH$_3$).

$^{13}$C-NMR (100 MHz, CDCl$_3$, δ in ppm): 137.9 (N$_2$CH), 135.9 (p-phenyl-CH), 129.1 (phenyl-CH), 129.0 (CR$_3$), 126.8 (phenyl-CH), 120.5 (N—CH), 59.5 (N—CH—Ph), 20.45 (CH$_3$).

Mass spectrum (FAB): m/e=589.2 ([M$^+$+M−Cl], 4.14), 277 ([M$^+$−Cl], 100), 173 (13.6), 105 (43.8).

B) Preparation of 1,3-di[(S) −1'-phenylethyl]imidazolin-2-ylidene (10)

3.12 g (10 mmol) of 1,3-di-(S)-1'-phenylethylimidazolium chloride (10a) are deprotonated in accordance with the general description in a mixture of 20 ml of THF and 100 ml of NH$_3$ using 260 mg (10.8 mmol) of NaH. The substrate is sparingly soluble and only during the course of the reaction does a clear yellow solution form. After removing the ammonia, the mixture is made up with THF to 40 ml and the solution thus obtained is used further without further work-up.

$^{13}$C-NMR (100 MHz, THF, CD$_3$NO, δ in ppm): 211.2 (C:), 144.3 (phenyl-CR), 128.3, (phenyl-CH), 127.1 (p-phenyl-CH), 126.6 (phenyl-CH), 117.8 (N—CH=), 59.5 (N—CH) 22.3 (CH$_3$).

C) Preparation of 1,3-di[(S)-1'-phenylethyl]imidazole-2-thione (10b)

In a Schlenk tube, 80 mg (2.5 mmol) of sulfur are suspended in 10 ml of degassed THF. While stirring, 10 ml (2.5 mmol) of 0.25 M carbene solution (10) are added dropwise and the reaction mixture is stirred for 1 hour. The solvent is removed under reduced pressure, the residue is dissolved in methylene chloride and filtered. After concentrating the mother liquor, the product can be obtained by slow cooling in the form of colorless crystals. Yield: 690 mg (89%).

$^1$H-NMR (400 MHz, CDCl$_3$, δ in ppm): 7.3–7.1 (overlapping multiplets, 10H, Ph—CH), 6.53 (s, 2H, =C—H), 6.30 (q, J=7 Hz, 2H, CH), 1.66 (d, J=7 Hz, 6H, CH$_3$).

$^{13}$C-NMR (100 MHz, CDCl$_3$, δ in ppm): 161.6 (C=S), 140.0 (Ph—CR), 128.41 (Ph—CH), 27.35 (p-Ph—CH), 126.6 (Ph—CH), 114.3 (=CH), 54.7 (CH), 19.1 (CH$_3$).

Elemental analysis (in % by weight): Calculated: C 73.99 H 6.54 N 9.08 Found: C 74.06 H 6.51 N 9.14.

D) Preparation of pentacarbonyl{1,3-di[(S)-1'-phenylethyl]imidazolin-2-ylidene}tungsten (10c)

A Schlenk tube is charged with 880 mg (2.5 mmol) of hexacarbonyltungsten in 10 ml of degassed THF. While stirring, 10 ml (2.5 mmol) of 0.25M carbene solution (10) are added dropwise and the reaction mixture is stirred for a few hours. The solvent is removed under reduced pressure and any hexacarbonyltungsten still present is sublimed off overnight at room temperature.

The residue is dissolved in methylene chloride and filtered. After removing part of the methylene chloride under reduced pressure, the product can be obtained by slow cooling in the form of yellow crystals. Yield: 945 mg (63%).

$^1$H-NMR (400 MHz, C$_6$D$_6$, δ in ppm): 7.14–7.29 (overlapping multiplets, 10H, Ph—CH), 6.48 (g, J=3 Hz, 2H, N—CH—Ph), 6.28 (s, 2H, CH=), 1.55 (d, J=6.5 Hz, 6H, CH$_3$).

$^{13}$C-NMR (100 MHz, C$_6$D$_6$, δ in ppm): 200.9 (trans-CO), 198.5 (cis-CO), 180.3 (CN$_2$), 141.2 (p-Ph—CN), 129.4 (Ph—CH), 128.6 (Ph—CR), 127.1 (Ph—CH), 120.4 (=CH), 60.9 (CH), 21.7 (CH$_3$).

E) Preparation of chloro(η$^4$-1,5-cyclooctadiene){1,3-di[(S)-1'-phenylethyl]imidazolin-2-ylidene}rhodium (10d)

A Schlenk tube is charged with 200 mg (0.4 mmol) of bis[(μ-chloro)(η$^4$-1,5-cyclooctadien)rhodium] in 5 ml of THF. To this solution, 3.3 ml (0.8 mmol) of carbene solution (10) are slowly added by means of a syringe.

The reaction mixture is stirred further for 1 hour at room temperature, the solvent is then removed under reduced pressure, the residue is taken up in methylene chloride and filtered. The complex is precipitated by addition of pentane and washed with pentane. Removing the volatile constituents under reduced pressure gives the complex as a yellow powder. Yield: 327 mg (79%).

1H-NMR (400 MHz, CDCl$_3$ δ in ppm): 7.66–7.25 (overlapping multiplets, 10H, Ph—CH), 6.91 (q, J=7 Hz, 1H, N—CH—Ph), 6.89 (q, J=7 Hz, 1H, N—CH—Ph), 6.82 (d, J=2 Hz, N—CH=), 6.65 (d, J=2 Hz, N—CH=), 5.06 (m, 2H, COD—CH), 3.45 (m, 1H, COD—CH), 3.21 (m, 1H, COD—CH), 2.5–2.3 (m, 4H, COD—CH$_2$), 2.2–1.8 (overlapping multiplets, 4H, COD—CH$_2$), 1.91 (d, J=7 Hz, 3H, CH$_3$, 1.83 (d, J=7 Hz, 3H, CH$_3$).

$^{13}$C-NMR (100 MHz, CDCl$_3$, δ in ppm): 182.0 (d, J(Rh—$^{13}$C)=51 Hz, Rh—CN$_2$), 142.2 (Ph—CR), 140.2 (Ph—CR), 128.8 (Ph—CH), 128.6 (Ph—CH), 127.9 (p-PhCH), 127.6 (Ph—CH), 126.2 (Ph—CH), 125.8 (p-Ph—CH), 118 (N—CH=), 118.2 (N—CH=), 98.5 (d, J(Rh—$^{13}$C)=7 Hz, COD—CH), 98.3 (d, J(Rh—$^{13}$C)=7 Hz, COD—CH), 68.7 (d, J(Rh—$^{13}$C)=14 Hz, COD—CH), 67.5 (d, J(Rh—$^{13}$C)=14 Hz, COD—CH), 59.7 (N—CH), 58.2 (N—CH), 33.0 (COD—CH$_2$), 32.7 (COD—CH$_2$), 28.7 (COD—CH$_2$), 22.8 (CH$_3$), 20.8 (CH$_3$).

Mass spectrum (CI): m/e=522 ([M$^+$], 38), 487 ([M$^+$−Cl], 100), 414 ([M$^+$−COD], 22), 378 ([M$^+$−COD−Cl]), 277 (8), 137 (10).

Example 11

1-Methyl-3-(2-diphenylphosphinylethyl)imidazolin-2-ylidene (11)

A1) Preparation of 1-methyl-3-(2-diphenylphosphorylethyl)imidazolium iodide (11a)

13.2 g (49.9 mmol) of 2-chloro-1-diphenylphosphorylethane are, with addition of 7 ml (50 mmol) of triethylamine, reacted in a mixture of 50 ml of toluene and 30 ml of ethanol with 3.4 g (50 mmol) of imidazole. The mixture is refluxed for 5 hours. The resulting 1-imidazole-2-(diphenylphosphoryl)ethane is quaternized at room temperature with 3.13 ml (50 mmol) of methyl iodide. 1-methyl-3-(2-diphenylphosphorylethyl)imidazolium iodide is precipitated by addition of 100 ml of diethyl ether and dried under reduced pressure. This results in 15.7 g (65%) of (11a) as the monoethanol adduct.

1H-NMR (400 MHz, CDCl$_3$, δ in ppm): 8.9 (s, 1H, NC HN); 8.0–7.0 (m, 12H; Ph, NCHNCH); 4.5 (m, 2H, NCH$_2$); 3.6 (s, 3H, NCH$_3$); 3.2 (m, 2H, CH$_2$PO); 3.6; 1.1 (EtOH).

$^{13}$C-NMR (100.6 MHz, CDCl$_3$, δ in ppm): 136.68 (s, N CHN); 131.72 (d, J$_{CP}$=3 Hz), 131.4 (s), 130.10 (d, J$_{CP}$=9 Hz), 128.35 (d, J$_{CP}$=12 Hz, Ph), 122.66; 122.63 (s, NCHN CH); 43.43 (s, NCH$_2$); 36.31 (s, NCH$_3$); 29.97 (d, $^1$J$_{CP}$=69 Hz, CH$_2$PO); 50.0; 17.9 (EtOH). $^{31}$P-NMR (161.9 MHz, CDCl$_3$, δ in ppm): 28.47 (s).

Elemental analysis (C$_{18}$H$_{20}$N$_2$P$_1$O$_1$I$_1$) (in % by weight): Calculated: C 49.3 H 4.6 N 6.4 I 29.0 Found: C 47.8 H 4.7 N 6.1 I 29.0.

A2) Reduction of 1-methyl-3-(2-diphenylphosphorylethyl) imidazolium iodide (11a) to 1-methyl-3-(2-diphenylphosphoethyl)imidazolium iodide (11b)

10.0 g (22.8 mmol) of 1-methyl-3-(2-diphenylphosphorylethyl)imidazolium iodide (11a) in 50 ml of toluene are admixed with 20 ml (11.2 g, 97 mmol) of methyldichlorosilane and 10 ml of ethanol and heated at 140° C. for 48 hours. After cooling, the organic phase is decanted off, the white solid is washed with 20 ml of toluene and 20 ml of pentane and dried under reduced pressure. This results in 9.2 g of (11b).

1H-NMR (400 MHz, CDCl$_3$ δ in ppm): 9.8 (s, 1H, NC$\underline{H}$N); 7.5–7.0 (m, 12H; Ph, NC$\underline{H}$NC$\underline{H}$); 4.4 (m, 2H, NC$\underline{H}_2$); 3.95 (s, 3H, NC$\underline{H}_3$); 2.8 (M, 2H, C$\underline{H}_2$P).

$^{13}$C-NMR (100 MHz, CDCl$_3$, δ in ppm): 137.5 (s, N$\underline{C}$HN); 132.2 (d), 129.2 (s); 128.6 (d), 127.9 (d, Ph), 123.4; 122.2 (s, N$\underline{C}$HN$\underline{C}$H); 47.2 (d, $^2J_{CP}$=20 Hz, N$\underline{C}$H$_2$); 36.5 (s, N$\underline{C}$H$_3$); 28.8 (d, $^1J_{CP}$=8 Hz, $\underline{C}$H$_2$P). $^{31}$P-NMR (161.9 MHz, CDCl$_3$, δ in ppm): –19.8 (s).

B) Preparation of 1-methyl-3-(2-diphenylphosphinoethyl)imidazolin-2-ylidene (11)

As described in the general example, 10 mmol of the salt (11b) obtained under point 11A2) are deprotonated in a mixture of ammonia/THF by means of 11 mmol of NaH. Removal of the ammonia results in a spectroscopically pure solution of the free 1-methyl-3-(2-diphenylphosphinylethyl) imidazolin-2-ylidene (11) in THF.

$^{13}$C-NMR (100 MHz, THF/d$_8$-THF external reference, δ in ppm): 217.3 (s, N$\underline{C}$N); 132.1 (d), 129.4 (s); 128.6 (d), 127.6 (d, Ph), 122.3; 121.3 (s, N$\underline{C}$HN$\underline{C}$H); 48.2 (d, $^2J_{CP}$=20 Hz, N$\underline{C}$H$_2$); 37.5 (s, N$\underline{C}$H$_3$); 29.1 (d, $^1J_{CP}$=18 Hz, $\underline{C}$H$_2$P). $^{31}$P-NMR (161.9 MHz, THF/d$_8$-THF external reference, δ in ppm): 19.5 (s).

Example 12

Bis-2,6-(3,3'-dimethyl-1,1'-dimethyleneimidazol-2-ylidene)pyridine

A) Preparation of bis-2,6-(1,1'-dimethyleneimidazole) pyridine 4.0 g (37.0 mmol) of potassium imidazolide (cf. Example 3A) are suspended in 70 ml of toluene. 2.5 g (18.5 mmol) of 2,6-bis(bromomethyl)pyridine are added at 0° C. and the mixture is allowed to warm to room temperature while stirring. After a total reaction time of 12 hours, the mixture is freed of toluene under reduced pressure. To remove the potassium bromide, the residue is extracted a number of times with chloroform. The extract is freed of the solvent in a high vacuum. The product remains. Yield: 3.76 g (85%).

1H-NMR (400 MHz, 25° C., D$_2$O, δ in ppm): 7.72 (s, 2H), 7.53 (t, 1H), 7.08 (m, 4H), 6.93 (d, 2H), 5.10 (s, 4H).

$^{13}$C-NMR (100 MHz, 25° C., D$_2$O, δ in ppm): 155.9, 138.0, 137.8, 127.6, 123.1, 120.3, 51.4.

B) Preparation of bis-2,6-(3,3'-dimethyl-1,1'-dimethyleneimidazolium iodide)pyridine 3.5 g (14.6 mmol) of bis-2,6-(1,1'-dimethyleneimidazole) pyridine are dissolved in 20 ml of chloroform and admixed with 2.0 ml (32.0 mmol) of iodomethane. After a further reaction time of 12 hours, the precipitated, slightly yellowish solid is separated from the chloroform solution by filtration and dried in a high vacuum. Yield: 7.24 g (88%).

1H-NMR (400 MHz, 25° C., D$_2$O, δ in ppm): 8.67 (s, 2H), 7.81 (t, 1H), 7.36 (m, 4H), 7.34 (d, 2H), 5.37 (s, 4H), 3.80 (s, 6H).

$^{13}$C-NMR (100 MHz, 25° C., D$_2$O, δ in ppm): 153.24, 139.86, 136.88, 123.70, 123.22, 123.06, 53.41, 36.07.

Elemental analysis (in % by weight): Calculated: C 34.44 H 3.66 N 13.39 I 48.51 Found: C 34.20 H 3.59 N 13.44 I 48.76.

C) Preparation of bis-2,6-(3,3'-dimethyl-1,1'-dimethyleneimidazolium hexafluorophosphate)pyridine 5.0 g (9.55 mmol) of bis-2,6-(3,3'-dimethyl-1,1'-dimethyleneimidazolium iodide)pyridine are dissolved in 70 ml of water and admixed with 3.59 g (22.0 mmol) of ammonium hexafluorophosphate. The colorless precipitate which forms is filtered off and subsequently recrystallized from 70 ml methanol. Yield: 5.11 g (78%).

1H-NMR (400 MHz, 25° C., DMSO, δ in ppm): 9.07 (s, 2H), 7.97 (t, 1H), 7.65 (m, 4H), 7.45 (d, 2H), 5.51 (s, 4H), 3.88 (s, 6H).

$^{13}$C-NMR (100 MHz, 25° C., DMSO, δ in ppm): 153.57, 138.82, 137.18, 123.38, 123.12, 122.00, 52.56, 35.83.

Elemental analysis (in % by weight): Calculated: C 32.21 H 3.42 N 12.52 Found: C 32.28 H 3.36 N 12.40.

D) Preparation of bis-2,6-(3,3'-dimethyl-1,1'-dimethyleneimidazol-2-ylidene)pyridine 5.59 g (10.0 mmol) of bis-2,6-(3,3'-dimethyl-1,1'-dimethyleneimidazolium hexafluorophosphate)pyridine are dissolved in 15 ml of tetrahydrofuran. 75 ml of ammonia are condensed in. 22 mmol of NaH are added at –78° C. The slightly yellowish solution is stirred under reflux for about 1 hour until gas evolution has ended. The ammonia is subsequently allowed to evaporate. An immediate further work-up of the carbene solution is absolutely necessary, since otherwise the solution quickly becomes red and a dark red solid begins to precipitate.

$^{13}$C-NMR (100 MHz, 25° C., THF, δ in ppm): 200.81, 157.10, 138.11, 121.57, 120.50, 120.15, 55.05, 36.62.

Comparative Example

Preparation of 1,3-di-(S)-1'-phenylethylimidazolin-2-ylidene without addition of ammonia 3.12 g (10 mmol) of 1,3-di-(S)-1'-phenylethylimidazolium chloride are suspended in 200 ml of THF. With exclusion of air, 260 mg (10.8 mmol) of NaH and a spatula tip of potassium tert-butoxide are added. Slight evolution of gas occurs. As the reaction proceeds further, the NaH starts to form lumps together with the starting material and the reaction stops. On slowly warming this suspension, the reaction mixture becomes yellow and then brown. Significant constituents of the starting material are still present as a lump on the bottom of the reaction flask. After stirring for 3 hours at 45° C., a sample of the reaction solution is transferred with exclusion of air and moisture into an NMR tube with nitromethane-d$_6$ external reference and is examined by NMR spectroscopy. A complicated mixture of signals which cannot be assigned is observed.

Similar results are observed when the imidazolium salt is first boiled in THF until it is converted into a fluid oil and NaH is added only then.

Deprotonation using potassium tert-butoxide in acetonitrile leads to no appreciable conversion. An attempt to carry out the deprotonation using NaH in acetonitrile results in secondary reactions by deprotonation of the acetonitrile which lead to a dark brown coloration of the reaction mixture.

We claim:

1. A process for the preparation of a heterocyclic carbene of the formula

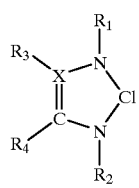

I wherein $R^1$, $R^2$, $R^3$ and $R^4$ are individually selected from the group consisting of unsubstituted or substituted alkylidene of 2 to 5 carbon atoms, unsubstituted or substituted alkylidine and alkylidyne of 2 to 5 carbon atoms, unsubstituted or substituted aryl of of 6 to 14 carbon atoms and unsubstituted or substituted aralkyl of 7 to 19 carbon atoms and $R^3$ and $R^4$ can be hydrogen or together with the carbon atoms to which they are attached form a fused on a group of 5 to 9 carbon atoms, the substituents being at least one member of the group consisting of halogen, $-NH_2$, $-NO_2$, $-CN$, isonitrile, $-OH$, $=O$, $-COOH$, $-CONH_2$, pyridyl and azolyl, X is carbon or nitrogen with the proviso that $R_3$ is not present when X is nitrogen comprising reacting at $-75°$ to $0°$ C. in the absence of air and moisture an azolium salt of the formula

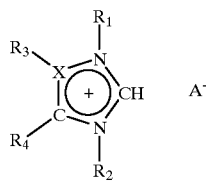

II wherein $R^1$, $R^2$, $R^3$ and $R^4$ are defined as above and A is selected from the group consisting of halide, pseudohalide, borate, phosphate, carboxylate and metal complex ion with a deprotonation agent in pure liquid ammonia or pure alkylamine of 1 to 4 carbon atoms liquid at the reaction temperature or a mixture of pure ammonia and said pure alkylamine and an organic polar aprotic solvent.

2. The process of claim 1 wherein $R^1$, $R^2$, $R^3$ and $R^4$ are individually selected from the group consisting of alkyl of 1 to 6 carbon atoms, alkylidene of 2 to 4 carbon atoms, alkylidyne of 2 to 4 carbon atoms, phenyl and phenylalkyl of 7 to 10 carbon atoms.

3. The process of claim 1 wherein one of $R^1$ and $R^2$ is substituted with pyridyl or an azolium salt.

4. The process of claim 1 wherein the alkylamine is methylamine or ethylamine.

5. The process of claim 1 wherein the reaction is effected at $-50$ to $-30°$ C.

6. The process of claim 1 wherein the organic polar aprotic solvent is selected from the group consisting of tetrahydrofuran, dimethylsulfoxide and acetonitrile and the volume ratio of ammonia and/or alkylamine to said solvent is 1:0.01 to 1:100.

7. The process of claim 6 wherein the volume ratio is about 1:0.2.

8. The process of claim 1 wherein the deprotenation agent is selected from the group consisting of metal hydroxides, metal amides, metal alkoxides, methyl carboxylates, carbonylmetallates and hydrido(carbonyl)-metallates in an at least stoichiometric amounts based on the compound of Formula II.

9. The process of claim 8 wherein the deprotonation agent is selected from the group consisting of sodium hydride and potassium amide in a 10% molar excess based on the compound of Formula II.

* * * * *